United States Patent [19]

Schwartz et al.

[11] Patent Number: 4,803,217

[45] Date of Patent: Feb. 7, 1989

[54] HAPALINDOLINONE COMPOUNDS AS VASSOPRESSIN ANTAGONISTS

[75] Inventors: Robert E. Schwartz, Westfield; Charles F. Hirsch, Sommerville; Janet M. Sigmund, Linden, all of N.J.; Douglas J. Pettibone, Chalfont, Pa.

[73] Assignee: Merck & Co., Inc., Rahway, N.J.

[21] Appl. No.: 946,545

[22] Filed: Dec. 24, 1986

[51] Int. Cl.$^4$ .................. C07D 209/96; A61K 31/40; C12P 17/10

[52] U.S. Cl. .................................. 514/409; 435/121; 548/411

[58] Field of Search ........................ 514/409; 548/411

[56] References Cited

U.S. PATENT DOCUMENTS 4,622,336 11/1986 Achini .................. 548/411

FOREIGN PATENT DOCUMENTS 171283 2/1986 European Pat. Off. .

OTHER PUBLICATIONS

Can. J. Physiol. Pharmacol 61: 1226-1235 (1983); McNeil, J. R.
Federation Proceedings 42: 3170-3176 (1983); Cowley, et al.
Federation Proceedings 43: 87-90 (1984) Sawyer & Manning.
Ann. Rev. Med. 31: 315-327 (1980) Zerbe, et al.
J. Med. Chem. 28: 1759-1760 (1985) Huffman, et al.
Federation Proceedings 45: 205 (1986); Lynn, et al.
Federation Proceedings 45: 649 (1986); Kinter, et al.
J. Am. Chem. Soc. 106: 6456-6457 (1984); Moore et al.
Moriconi et al., *J. Org. Chem.* 29, p. 3577 (1964).

*Primary Examiner*—Mark L. Berch
*Assistant Examiner*—F. Bernhardt
*Attorney, Agent, or Firm*—Hesna J. Pfeiffer; Charles M. Caruso

[57] ABSTRACT

Hapalindolinone compounds are produced by the controlled aerobic fermentation of a cyanobacterium of the genus Fischerella, ATCC No. 53558. These compounds are antagonists of vasopressin and are useful in the treatment and prevention of disease states wherein vasopressin may be involved, for example congestive heart failure, hypertension, edema and hyponatremia, and have the formula:

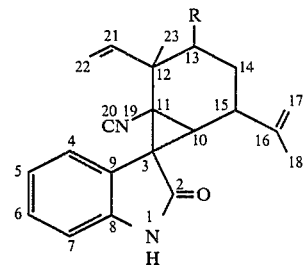

IA R = Cl
IB R = H

5 Claims, 1 Drawing Sheet

HAPALINDOLINONE COMPOUNDS AS VASSOPRESSIN ANTAGONISTS

BACKGROUND OF THE INVENTION

This invention pertains to the field of vasopressin antagonists. Vasopressin (also known as Antidiuretic Hormone, ADH) is a pituitary peptide hormone that is vital for the maintenance of proper water balance in animals and man. The antidiuretic effect of vasopressin concentrates the urine by increasing the reabsorption of water from the kidney filtrate. Thus, even under mild conditions of dehydration enhanced blood levels of vasopressin act to conserve water and control the proper osmolarity of the blood and extracellular fluids. Vasopressin also acts to contract vascular smooth muscle and may normally be involved in the maintenance of peripheral vascular resistance (McNieil, J.R., Can. J. Physiol Pharmacol 61: 1226–1235 (1983); Cowley, A.W., Quillen, E.W., and Skeleton, M.M., Federation Proceedings 42: 3170–3176 (1983)).

Recent studies have led to the development of relatively potent and specific antagonists of the antidiuretic or pressor effects of vasopressin (Sawyer, W.H., and Manning, M., Federation Proceedings 43: 87–90 (1984)). Because of the prominent actions of vasopressin on renal and cardiovascular function, vasopressin antagonists are useful in the treatment of several conditions including congestive heart failure, hypertension, and states of edema. The salt-sparing, 'water diuretic' activity of vasopressin antagonists would be particularly useful in the treatment of hyponatremia which can arise from a variety of conditions (Zerbe, R., Stropes, L., Robertson, G., Ann. Rev. Med. 31: 315–327 (1980)). The currently known vasopressin antagonists are peptide analogues of vasopressin (Huffman, W.H., Ali, F.E., Bryan, W.M. et al. J. Med Chem 28: 1759–1760 (1985)) and are, therefore, likely to be rapidly metabolized in vivo and to have little, if any, oral activity (Lynn, R.K., Straub, K.M., Landvatter, S.W., and Garvey, C.T., Federation Proceedings 45: 205 (1986); Kinter, L.B., Mann, W.A., Woodward, P., DePalma, D. and Brennan, F., Federation Proceedings 45: 649 (1986)).

The non-peptide structure of the hapalindolinone compounds of the present invention would increase the likelihood of oral absorbtion and activity in comparison to known vasopressin antagonists of peptide structure (See Lynn et al. 1986; Kinten et al. 1986).

In addition, some hapalindole compounds having structures somewhat related to the compounds of the present invention have been reported as being useful as antibacterial and antifungal agents in EP Application 171,283 and Moore et al., J. Am. Chem. Soc. 106: 6456-57 (1984). There is, however, no suggestion that any of the fermentation products disclosed therein would be of use as vasopressin antagonists. Moreover, those compounds are structurally distinct from the compounds of the present invention.

It is, therefore, an object of the present invention to provide hapalindolinone compounds which are antagonists of vasopressin and are useful as pharmaceutical agents. It is also an object of the present invention to provide processes for producing these hapalindolinone compounds. It is a further object of the invention to provide a mixture of hapalindolinone compounds, called Hapalindolinone A and Hapalindolinone B (Formula IA and IB), produced by aerobic fermentation of a cyanobacterium of the genus Fischerella. A still further object is to provide cultures of the cyanobacterium of the genus Fischerella ATCC No. 53558 which are capable of producing hapalindolinone compounds and mixtures thereof.

BRIEF DESCRIPTION OF THE DRAWING

The FIGURE is a perspective drawing of the compound of Formula IA showing the absolute sterochemistry. The numbering coincides with the numbering system of the planar representation.

SUMMARY OF THE INVENTION

Figure 1:
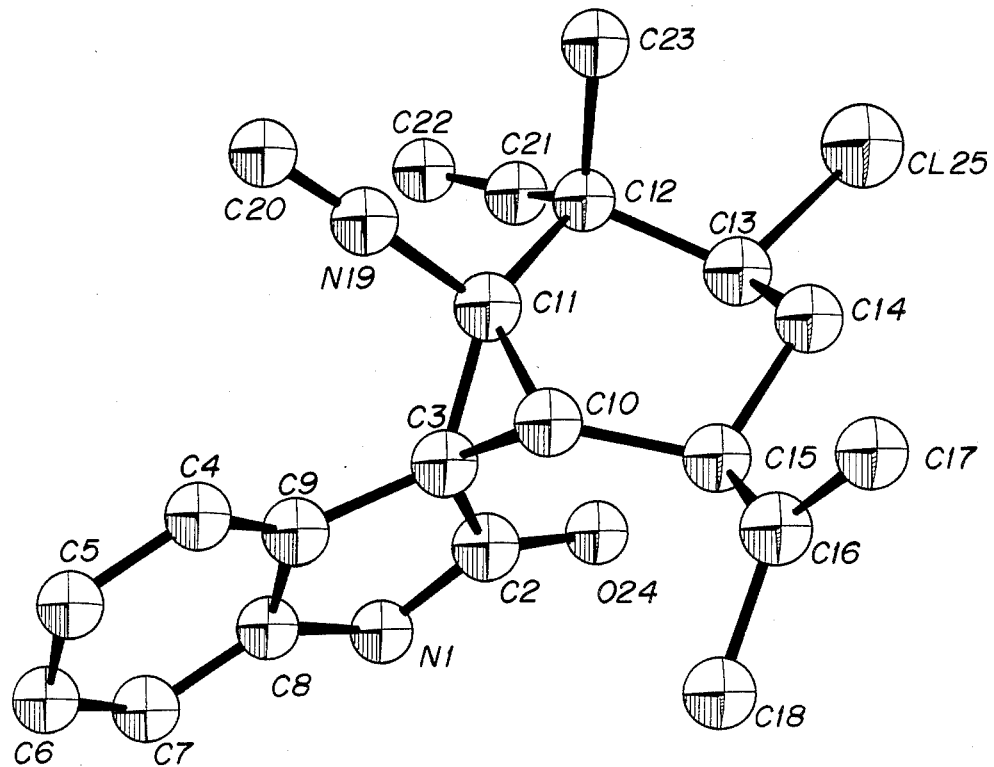

It has now been found that the compounds of Formula IA and IB, Hapalindolinone A and B, are produced by the controlled aerobic fermentation of a cyanobacterium of the genus Fischerella ATCC No. 53558.

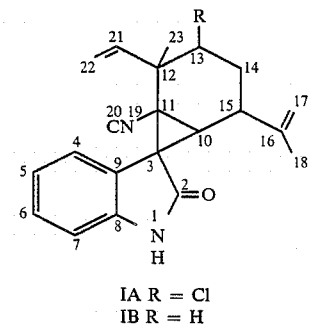

IA R = Cl
IB R = H

The compounds of Formula IA and IB are antagonists of vasopressin. Vasopressin antagonists are useful in the treatment and prevention of disorders of the renal and cardiovascular system of animals, including humans. The preparation and isolation of the compounds of Formula IA and IB is described. Also described is the activity of the compounds of Formula IA and IB as antagonists of vasopressin.

DETAILED DESCRIPTION

The compounds of Formula IA and IB are produced by the controlled aerobic fermentation of a cyanobacterium of the genus Fischerella, ATCC No. 53558.

The cyanobacterium ATCC No. 53558 was isolated from a soil taken from a swampy area in southern Florida (the Everglades, Florida). A deposit under the Budapest Treaty of a biologically pure culture of this cyanobacterium was made with the American Type Culture Collection, Rockville, Md., on Dec. 5, 1986 under Accession No. ATCC 53558.

This cyanobacterium is filamentous and exhibits true branching and a complex developmental cycle. The culture tolerates storage in liquid $N_2$ (10% glycerol cryoprotectant) for at least 2 months. Based on its morphological characteristics, this culture appears to be a member of typological gropu V in the genus Fischerella, as defined by Rippka et al., J. Gen. Microbiol. 111: 1–61 (1979).

FERMENTATION CONDITIONS

The compounds of Formula IA and IB are produced by the aerobic fermentation of suitable aqueous nutrient media under controlled conditions via inoculation with a culture of the cyanobacterium of the genus Fischerella, ATCC No. 53558. The media contain sources of assimilable carbon, nitrogen, and inorganic salts.

Among the nutrient inorganic salts which can be incorporated in the culture medium are customary salts capable of yielding sodium, potassium, nitrate, calcium, phosphate, sulfate, chloride, carbonate, and the like ions. Also included are trace metals such as cobalt, manganese, iron, magnesium, and the like.

It should be noted that the nutrient medium described herein is merely illustrative of the wide variety of media which may be employed, and is not intended to be limiting.

The fermentation is carried out at temperatures ranging from about 25° C. to 30° C.; however, for optimum results it is preferable to conduct the fermentation at temperatures of about 28° C. The pH of the nutrient medium for growing the cyanobacterium of the genus Fischerella, ATCC No. 53558, cultures and producing the vasopressin antagonists of Formula IA and IB can vary from about 7 to 8. The fermentation is carried out under a light intensity of 3500-5000 lux.

It is to be understood that for the fermentation production of the compounds of Formula IA and IB, the present invention is not limited to the use of cyanobacterium of the genus Fischerella, ATCC No. 53558. It is especially desired and intended that there be included within the scope of this invention the use of other natural or artificial mutants produced or derived from the described cultures, or other variants or species of the genus Fischerella insofar as they can produce the compound of Formula IA and IB. The artificial production of mutant species or strains of Fischerells from ATCC No. 53558 may be achieved by conventional, physical or chemical mutagens, for example, ultraviolet irradiation of the described cultures, or nitrosoguanidine treatment and the like. Recent recombinant DNA techniques such as protoplast fusion, plasmid incorporation, chromosome fragment incorporation and the like may also prove useful.

In a preferred embodiment of the present invention, the compounds of Formula IA and IB are produced by the controlled aerobic fermentation of the cyanobacterium of the genus Fischerella ATCC No. 53558. Fermentation should be conducted at a temperature range of from about 25° C. to 30° C., preferably at about 28° C. The essential nutrient ingredients are a carbon source and a nitrogen source. Other essential nutrients are provided via mineral salts such as the chlorides, nitrates, sulfates, carbonates and phosphates of sodium, potassium and calcium. The nutrient medium may also contain courses of inorganic trace elements such as magnesium, iron, copper, manganese, zinc, cobalt, and the like.

Typical sources of carbon include: carbon dioxide and bicarbonate. Typical nitrogen sources include sodium nitrate or potassium nitrate.

The maximum yield of the compounds of Formula IA and IB can be achieved within about 12 to 20 days, usually in about 14 to 17 days, of fermentation under optimum conditions. The inoculum for the fermentation may be provided from vegetative growth in a medium which supports rapid growth of the micro-organism.

Following fermentation, the accumulated compounds of Formula IA and IB may be separated from related compounds and recovered from the broth by conventional chromatographic means.

The fermentation broth is filtered to separate cells from liquid supernatant. These are extracted as follows:

The cells are stirred vigorously (homogenized) with several volumes of methanol, acetone, ethyl acetate, methyl ethyl ketone or the like. These solvents will dissolve most of the compounds of Formula IA and IB located within the cells.

The cellular organic extracts are then concentrated to a small volume under reduced pressure. The resultant mass is subjected to solvent partitioning with a solvent such as methylene chloride, followed by drying and concentration.

Adsorption and partition chromatographies, gel filtration, reversed-phase liquid chromatogrpahy and the like may be used, in conjunction with eluant of proper polarity and solubilizing characteristics to afford the compounds of Formula IA and IB.

A number of different nutrient media may be employed in the fermentation of a cyanobacterium of the genus Fischerella, ATCC No. 53558. Variation of the medium or the microorganism will vary the yield of the compounds of Formula IA and IB and/or its rate of production. Variation of the medium or the microorganism may also increase or decrease the type and amount of the compounds present in the broth. The preferred medium compositions are set forth in Table I.

TABLE I

| MEDIA | |
|---|---|
| BG-12 | |
| $NaNO_3$ | 1.5 g/L |
| $K_2HPO_4$ | 0.031 g/L |
| $MgSO_4.7H_2O$ | 0.075 g/L |
| $CaCl_2.2H_2O$ | 0.036 g/L |
| Citric acid | 0.006 g/L |
| Ferric Ammonium Citrate | 0.006 g/L |
| EDTA ($Na_2Mg$ salt) | 0.001 g/L |
| $Na_2CO_3$ | 0.02 g/L |
| Trace element solution | 1.0 ml/L |
| HEPES (4-(2-Hydroxyethyl)-1-piperzine-ethanesulfonic acid available from Boehringer Mannheim Biochemicals) | 1.2 g/L |
| pH 8.5 | |
| Trace element solution | |
| $H_3BO_3$ | 2.86 g/L |
| $MnCl_2.4H_2O$ | 1.81 g/L |
| $ZnSO_4.7H_2O$ | 0.222 g/L |
| $Na_2MoO_4.2H_2O$ | 0.390 g/L |
| $CuSO_4.5H_2O$ | 0.079 g/L |
| $CoCl_2.6H_2O$ | 0.040 g/L |

The terms "seed" and "production" media are employed as terms of art. Generally, a seed medium supports rapid growth of the microorganism and an aliquot (seed) of this medium is used to inoculate a production medium for a large scale fermentation.

The following examples describe the fermentation production and isolation of the compounds of Formula IA and IB. These examples are merely illustrative, they are not intended to limit the scope of the invention.

EXAMPLE 1

The cells from a 3-week seed culture (25 mil) of ATCC No. 53558 were used to inoculate an active production culture (250 ml) which was incubated for 31 days prior to harvest. Both the seed and production cultures were grown at 28° C., 100-180 rpm in BG-12 medium (initial pH 8.5) at a light intensity of ~3500 lux under a continuously replenished atmosphere of 5% $CO_2$ in air. The headspace of the production flask was flushed with humidified gas at a flow rate of 200 ml/min.

EXAMPLE 2

The first regrowth was performed in a modified 2.8 L Fernbach flask containing 1 L of BG-12 medium using the incubation conditions previously described. Inoculum was prepared by inoculating cells from an agar slant culture of ATCC No. 53558 into 50 ml of BG-12 medium. After 11 days incubation, the cells from 50 ml were transfe4rred to 200 ml of BG-12 medium and incubated for 4 days. The cells then were harvested by centrifugation, resuspended in 10 ml of BG-12 medium and 5 ml of this cell suspension was used to inoculate the regrowth culture. After 17 days incubation, the regrowth culture was harvested.

EXAMPLE 3

The fermentation batch from Example 2 was centrifuged and the cell pellet extracted with 100 ml MeOH (3X). The MeOH extracts were filtered, concentrated to 100 ml and extracted with $CH_2Cl_2$ (100 ml, 2X). The $CH_2Cl_2$ extracts were combined, dried and concentrated to give 87.3 mg. This concentrate was chromatographed on a 40 ml Kieselgel 60 (230–400 mesh) silica gel comumn using $CH_2Cl_2$ as the solvent and a flow rate of 2 ml/min. A 10 ml void volume was discarded and 2 ml fractions collected and combined based on TLC (silica gel, $CH_2Cl_2$). The results are described in the table below.

TABLE II

| Component | $R_f$ | Mass |
|---|---|---|
| Formula IA | 0.39 | 18 mg |
| Formula IB | 0.25 | 7 mg |

Formula IA component was essentially pure at this point. Component IB was further purified via Sephadex LH-20 ($CH_2Cl_2$/hexane/MeOH, 10:10:1) chromatography.

EXAMPLE 4

Formula IA was further characterized via retention time using analytical HPLC in a variety of solvent systems. HPLC experiments were run on a DuPont Zorbax ODS 4.6 mm×25 cm column, 40° C., 1 ml/min. UV detection was utilized at 260 nm, attenuation 0.16×4. Retention times are shown in the table below.

TABLE III

| Component | Solvent (MeOH/0.1 M potassium phosphate buffer pH = 7) | Retention Time (minutes) |
|---|---|---|
| Formula IA | 95/5 | 3.50 |
| Formula IA | 90/10 | 4.36 |
| Formula IA | 85/15 | 5.86 |
| Formula IA | 80/20 | 8.43 |
| Formula IA | 70/30 | 22.51 |

CHARACTERIZATION OF THE COMPOUNDS OF FORMULA IA AND IB

The solid material obtained in Example 3 above was characterized by infrared spectrometry, high resolution mass spectrometry and nuclear magnetic resonance spectroscopy and X-ray diffraction as discussed below. From this data, the structures of Formula IA and IB were assigned. All possible steroisomers are encompassed by the structures shown below.

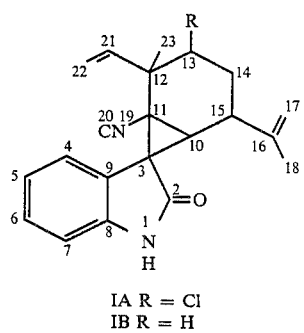

IA R = Cl
IB R = H

FORMULA IA COMPOUND

The IR spectrum of this compound contained adsorbances for the isonitrile (2125 cm$^{-1}$) and NH groups (3420 cm$^{-1}$), as well as a carbonyl band at 1716 cm$^{-1}$. The mass spectrum showed that this compound also contains a Cl atom and indicated a molecular formula of $C_{21}N_{21}N_2OCl$ (Calc. 352.1342, Found: 352.1347, unsaturations=12). NMR data is shown in Tables IV and V below.

FORMULA IB COMPOUND

The IR spectrum of IB is similar to that of IA with adsorbances at 2135 cm$^{-1}$ for the isonitrile, 3430 cm$^{-1}$ for the NH and 1719 cm$^{-1}$ for the carbonyl groups. The absence of the Cl was apparent in the $^1$Hv and $^{13}$C NMR spectra, (Table IV and V) as well as the MS (Found 318.1732, Calc 318.1732 for $C_{21}H_{22}N_2O$).

TABLE IV

| | $^1$H NMR$^a$ | | | |
|---|---|---|---|---|
| | IA | | IB | |
| 1 | 8.41 1 Hbs | | 7.85 1 Hbs | |
| 4$^b$ | 7.10–7.20 2 Hm | | 7.10–7.20 1 Hm | |
| 5$^b$ | 7.10–7.20 2 Hm | | 7.10–7.20 1 Hm | |
| 6$^b$ | 7.32 1 Hddd | J(6,7) = 7.7 | 7.28 1 Hddd | J(6,4) = 1.4 |
| | | J(6,5) = 7.4 | | J(6,5) = 7.7 |
| | | J(6,4) = 1.9 | | J(6,7) = 7.7 |
| 7$^b$ | 6.94 1 Hd | J(7,6) = 7.7 | 6.89 1 Hd | J(7,6) = 7.7 |
| 10 | 2.29 1 Hd | J(10,15) = 3.5 | 2.22 1 Hd | J(10,15) = 4.0 |
| 13$^c$ | 5.75 1 Hdd | J(13,14) = 9.3 | 2.86 1 Hddd | J(13,13) = −14.0 |
| | | J(13,14) = 6.7 | | J(13,14) = 14.0 |
| | | | | J(13,14) = 2.6 |
| 14 | 2.10 2 Hm | | 1.8–2.2 1 Hm | |
| | | | 1.6–2.1 2 Hm | |
| 15 | 3.14 1 Hddd | J(15,10) = 3.5 | 2.95 1 Hddd | J(15,10) = 4.0 |
| | | J(15,14) = 8.1 | | J(15,14) = 4.0 |

TABLE IV-continued

$^1$H NMR$^a$

| | IA | | IB | |
|---|---|---|---|---|
| | | J(15,14) = 8.1 | | J(15,14) = 12.7 |
| 17 | 4.91 1 Hbs | | 4.85 1 Hbs | |
| | 4.89 1 Hbs | | 4.82 1 Hbt | J(17,18) = 1.2 |
| 18 | 1.81 3 Hs | | 1.75 3 Hs | |
| 21 | 5.98 1 Hdd | J(21,22) = 17.6 | 5.84 1 Hdd | J(21,22) = 17.8 |
| | | J(21,22) = 10.9 | | J(21,22) = 10.8 |
| 22 | 5.14 1 Hd | J(22,21) = 10.9 | 4.96 1 Hd | J(22,21) = 10.8 |
| | 5.08 1 Hd | J(22,21) = 17.6 | 4.92 1 Hd | J(22,21) = 17.8 |
| 23 | 1.74 3 Hs | | 1.55 3 Hs | | b These protons are resolved in C$_6$D$_6$:
4  7.08 1 Hd    J(4,5) = 7.5
5  6.83 1 Hdd   J(5,4) = 7.5
                J(5,6) = 7.5
6  6.92 1 Hdd   J(6,5) = 7.5
                J(6,6) = 7.5
7  6.30 1 Hd    J(7,6) = 7.5
c These coupling constants are significantly different in C$_6$D$_6$:
13  6.13 1 Hdd  J(13,14) = 5.4
                J(13,14) = 15.7
a Spectra was recorded at 300 MHz in CDCl$_3$; chemical shifts are referenced to CDCl$_3$ at 7.24 Hz. Coupling constants are reported in Hz.

TABLE V

$^{13}$C NMR$^a$

| | IA | IB |
|---|---|---|
| 2 | 173.98 C | 173.50 C |
| 3 | 40.23 C | 38.17 C |
| 4 | 122.42 CH J = 163 | 121.73 CH |
| 5 | 123.40 CH J = 161 | 123.10 CH |
| 6 | 128.55 CH J = 162 | 128.08 CH |
| 7 | 109.45 CH J = 163 | 109.03 CH |
| 8 | 139.51 C | 139.70 C |
| 9 | 126.03 C | 126.64 C |
| 10 | 39.76 CH J = 164 | 40.99 CH |
| 11 | 57.36 C | 55.50 C |
| 12 | 44.85 C | 39.64 C |
| 13 | 60.50 CH J = 150 | 24.82 CH$_2$ |
| 14 | 34.62 CH$_2$ J = 132 | 32.82 CH |
| 15 | 36.77 CH J = 131 | 36.09 CH |
| 16 | 145.71 C | 147.61 C |
| 17 | 112.22 CH$_2$ J = 156 | 111.16 CH$_2$ |
| 18 | 21.28 CH$_3$ J = 124 | 22.96 CH$_3$ |
| 20 | 158.06 C | 156.73 C |
| 21 | 138.65 CH J = 156 | 142.81 CH |
| 22 | 115.60 CH$_2$ J = 158 | 112.61 CH$_2$ |
| 23 | 20.319 CH$_3$ J = 120 | 20.60 CH$_3$ | a Spectral were recorded at 75 MHz in CDCL$_3$; chemical shifts are in ppm referenced to CDCL$_3$; coupling constants are reported in Hz.

Suitable crystals of Formula IA for X-ray diffraction studies were formed from ethyl acetate with space group symmetry of P2$_1$ and cell constants of a=13.984(2)Å, b=8.950(2)Å, c=16.284(4)Å and β=110.63(2)° for Z=4 and a calculated density of 1.229 g/cm$^3$. Of the 2754 reflections measured with an automatic four circle diffractometer equipped with Cu radiation, 2564 were observed (I>3σI). The structure was solved with a multi-solution tangent formula approach and difference Fourier analysis and refined using full-matrix least-squares techniques (The following library of crystallographic programs was used: MULTAN 80, P. Main, University of York, York, England (1980); ORTEP-II, C. K. Johnson, Oak Ridge National Laboratory, Oak Ridge, Tenn. (1970); SDP Plus V1.1, Y. Okaya and B. A. Frenz, B. A. Frenz and associates, College Station, Tex. (1984)). The absolute configuration was determined from anomalous scattering with one enantiomer giving an R factor of 0.079 while the other gave 0.085. This difference was significant at the 0.001 level (Hamilton, W.C. Acta Cryst., 1965, 18,502–510) and was confirmed by careful remeasurement of 10 enantiomorph sensitive reflections. Hydrogens were assigned isotropic temperature factors corresponding to their attached atoms. The function $\Sigma w(|Fo|-|Fc|)^2$ with $w=1/(\sigma Fo)^2$ was minimized to give an unweighted residual of 0.054. No abnormally short intermolecular contacts were noted. The drawing in this case is a computer generated perspective drawing of Formula IA from the final X-ray coordinates showing the absolute sterochemistry.

IN VITRO VASOPRESSIN ANTAGONISM

The biological activity of the compound of Formula IA is shown in Table VI, below. The table summarizes the in vitro potency of the compound to compete for $^3$H-vasopressin binding at two proposed vasopressin receptor subtypes (V$_1$, V$_2$), as well as to inhibit vasopressin-stimulated adenylate cyclase-activity, a further measure of vasopressin antagonism.

The [$^3$H]Arginine Vasopressin Binding Assay is an in vitro procedure which was adapted from the method of Guillon et al., Eur. J. Pharmacol. 85: 219–304 (1982). It measures the relative affinity of the compound for vasopressin receptor(s) labelled by [$^3$H]vasopressin. Vasopressin receptors have been divided into two subtypes pharmacollogically: the V$_1$(pressor)-receptor found in liver and vascular smooth muscle and the V$_2$(antidiuretic) receptor found in kidney medulla. The binding assay uses a crude membrane preparation of rat liver (V$_1$ receptor) or kidney medulla (V$_2$ receptor) which is incubated with [$^3$H]vasopressin in the presence or absence of the test compound. The IC$_{50}$ values (concentrations to inhibit [$^3$H]vasopressin binding by 50%) for the compound (see Table VI) are measures of their potencies and are inversely related to their affinities.

Vasopressin exerts its antidiuretic effects on the kidney through the stimulation of adenylate cyclase activity. Vasopressin-stimulated adenylate cyclase in kidney medulla, therefore, is used as a functional assay to determine the potencies of the test compound as V$_2$-vasopressin antagonists. In this assay, the IC$_{50}$ value obtained for the compound IA (see Table IV) is a measure of its potency to inhibit the vasopressin-stimulated conversion of ATP to CAMP by adenylate cyclase. This method was adapted from Seamon et al., PNAS 78: 3363–3367 (1981).

TABLE VI

| | IC$_{50}$ Values ($\mu M$)[a] | | |
| --- | --- | --- | --- |
| | $^3$H—Arg$^8$-Vasopressin Binding | | AVP-stimulated Ad, Cyclase |
| Compound | Liver (V$_1$) | Kidney (V$_2$) | Kidney (V$_2$) |
| Formula IA | >100$\mu$ (n = 3) | 37.5 ± 7.6 $\mu$M (n = 3) | 44.6 $\mu$M (n = 2) |

[a]Mean values with standard errors, as appropriate

The ability of the compounds of Formula IA and IB to antagonize vasopressin makes these compounds useful as pharmaceutical agents. These compounds will be especially useful in the treatment and prevention of disease states wherein vasopressin may be involved, for example, congestive heart failure, hypertension edema and hyponatremia.

The compounds of Formula IA and IB can be administered to a human subject either alone, or preferably, in combination with pharmaceutically acceptable carriers or dilutents, in a pharmaceutical composition, according to standard pharmaceutical practice. The compounds can be administered orally or parenterally. Parenteral administration includes intravenous, intramuscular, intraperitoneal, subcutaneous and topical administration.

For oral use of a vasopressin antagonist of this invention, the selected compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful dilutents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When the compounds of Formula IA and IB are used as a vasopressin antagonist in a human subject, the daily dosage will normally be determined by the prescribing physician. Moreover, the dosage will vary according to the age, weight and response of the individual patient, as well as the severity of the patient's symptoms. However, in most instances, an effective daily dosage will be in the range from about 1 mg to about 1500 mg and preferably 10 l mg to 500 mg in a single or divided doses. On the other hand, it may be necessary to use dosages outside these limits in some cases.

What is claimed is:

1. The compounds having the Formula IA and IB:

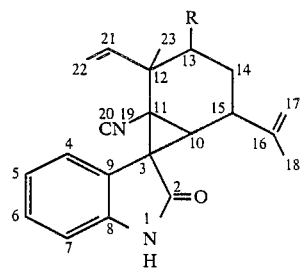

IA R = Cl
IB R = H

2. Hapalindolinone A having the empirical formula C$_{21}$H$_{21}$N$_2$OCl.

3. Hapalindolinone B having the empirical formula C$_{21}$H$_{22}$N$_2$O.

4. The mixture of the compounds of Formula IA and Ib as defined in claim 1 produced by controlled aqueous aerobic fermentation of a cyanobacterium of the genus Fischerella, ATCC No. 53558, in an aqueous nutrient medium.

5. A method of antagonizing vasopressin in animals which comprises administering an effective amount of a compound according to claim 1.

* * * * *